United States Patent [19]

di Salle et al.

[11] 4,151,283

[45] Apr. 24, 1979

[54] 6-METHYL-AND 1,6-DIMETHYL-8β-CARBOBENZYLOXY-AMINOMETHYL-10α-ERGOLINE AS INHIBITORS OF PROLACTIN SECRETION

[75] Inventors: Enrico di Salle; Claudio Praga; Erminia Castegnaro, all of Milan, Italy

[73] Assignee: Società' Farmaceutici Italia S.p.A., Milan, Italy

[21] Appl. No.: 810,872

[22] Filed: Jun. 28, 1977

[30] Foreign Application Priority Data

Feb. 17, 1977 [GB] United Kingdom ................. 6581/77

[51] Int. Cl.$^2$ ............................................. A61K 19/48
[52] U.S. Cl. ..................................................... 424/261
[58] Field of Search ......................................... 424/261

[56] References Cited

U.S. PATENT DOCUMENTS

| 3,238,211 | 3/1966 | Camerino et al. | 424/250 |
|---|---|---|---|
| 3,992,385 | 11/1976 | Bach et al. | 424/261 |

OTHER PUBLICATIONS

Masala et al.–Brit. Med. J., vol. 1, (1977), pp. 744–746.
Chiodini et al.–J. of Clinical Endocrin. and Metabolism, vol. 43, No. 3 (1976), p. 356.
Masala et al.–J. of Clinical Endocrin. and Metabolism, vol. 43, No. 3, (1976), pp. 1382–1386.
Masala et al.–Biomedicine, vol. 27, No. 10, (1976), pp. 31–33.
Pontiroli et al.–Acta Endocrinologica, vol. 84, No. 1, (1977), pp. 36–43.

*Primary Examiner*—Sam Rosen
*Attorney, Agent, or Firm*—Stevens, Davis, Miller & Mosher

[57] ABSTRACT

A method is disclosed for inhibiting prolactin secretion in a female mammal which comprises administering to the mammal an effective dose of 6-methyl-8β-carbobenzyloxy-aminomethyl-10α-ergoline, or 1,6-dimethyl-8β-carbobenzyloxy-aminomethyl-10α-ergoline, or a pharmaceutically acceptable acid addition salt thereof.

1 Claim, No Drawings

6-METHYL- AND 1,6-DIMETHYL-8β-CARBOBENZYLOXY-AMINOMETHYL-10α-ERGOLINE AS INHIBITORS OF PROLACTIN SECRETION

This invention relates to a new use of 6-methyl- and 1,6-dimethyl-8β-carbobenzyloxy-aminomethyl-10α-ergoline as inhibitors of prolactin secretion.

6-Methyl- and 1,6-dimethyl-8β-carbobenzyloxy-aminomethyl-10α-ergoline are known 10α-ergoline derivatives, described and claimed in U.S. Pat. No. 3,238,211. See also Beretta C., Ferrini R. and Glaesser A. H., Nature 207, 421, 1965, in which 1,6-dimethyl-8β-carbobenzyloxy-aminomethyl-10α-ergoline is described as a potent long-lasting 5-hydroxytryptamine antagonist.

For brevity, 1,6,-dimethyl-8β-carbobenzyloxy-aminomethyl-10α-ergoline will be hereinafter called "metergoline" and 6-methyl-8β-carbobenzyloxy-aminomethyl-10α-ergoline will be hereinafter called "1-demethyl-metergoline".

The process for the preparation of these compounds is well known; see for example the above mentioned U.S. Pat. No. 3,238,211. The starting materials, are 6-methyl- and 1,6-methyl-8β-carbamido-10α-ergoline, called also dihydro-D-lysergamide I (Stoll and Hoffman, Helv. Chim. Acta 29, 635, 1946), and 1-methyl-dihydro-D-lysergamide I (Troxler and Hoffman, Helv. Chim. Acta 40, 1971, 1957). These are reduced to 6-methyl- and to 1,6-dimethyl-8β-aminomethyl-10α-ergoline, called also dihydro-D-lysergamine I and 1-methyl-dihydro-D-lysergamine I respectively, and subsequently acylated to give amide derivatives.

The reduction of dihydro-D-lysergamide I and 1-methyldihydro-D-lysergamide I is carried out by lithium aluminum hydride. The reaction may be carried out at room temperature, but is preferably completed in the warm, i.e., somewhat elevated temperatures. It is carried out in the presence of a solvent such as tetrahydrofuran.

The reduction products, dihydro-D-lysergamine I and 1-methyl-dihydro-D-lysergamine I respectively, are isolated as such in crystalline form by concentrating the reaction mixture and subsequent cooling.

The corresponding N-acyl derivatives are prepared by reacting the dihydro-D-lysergamine I or 1-methyl-dihydro-D-lysergamine I with a suitable acylating agent.

The following examples further illustrate the preparation of the two active compounds the use of which constitutes the present invention:

EXAMPLE 1

6-Methyl-8β-carbobenzyloxy-aminomethyl-10α-ergoline (1-demethyl-metergoline)

1 g of dihydro-D-lysergic acid amide I was dissolved in 160 ml of anhydrous tetrahydrofuran and then reacted, at room temperature, with about 1 g of lithium aluminum hydride. The reaction mixture was kept at room temperature for an hour, then it was refluxed for an hour and a half, and then about ⅔ of the solvent was distilled off.

The suspension was cooled with ice and the excess reagent was destroyed slowly by addition of ice and chloroform. Chloroform was added and the mixture filtered, and the filter was washed thoroughly with chloroform. The chloroform solution was washed three times with water and then distilled in vacuo. The crystalline residue was taken up with ether and filtered.

0.7 g of dihydro-D-lysergamine I, melting at 204°–207° C., was obtained. 3 g of dihydro-D-lysergamine I, called also 6-methyl-8β-aminomethyl-10α-ergoline, were dissolved in 30 ml of chloroform and 3 ml of anhydrous pyridine.

To the solution cooled to −10° C. and stirred, 3.3 ml of benzylchloroformate diluted in 10 ml of chloroform were added dropwise. The well-stirred reaction mixture was kept between −5° and 0° C. during the addition and then at +15° for a further 1 hour.

The reaction mixture was poured into a separatory funnel and thoroughly shaken twice with 30 ml of 3% aqueous sodium hydroxide, with saturated aqueous sodium bicarbonate solution, and finally with water.

The chloroform solution was dried over anhydrous sodium sulfate and evaporated to dryness in vacuo at 40° C. The oily residue was taken up in chloroform-ethanol and passed through a chromatographic column containing 30 g of kieselguhr. The column was then eluted with chloroform-acetone.

The collected eluates were evaporated in vacuo at 40° C., and the residue was crystallized from acetone. M.P. 146°–148° C. $[\alpha]_D^{20} = -72°$ (c=0.5 in pyridine) $\lambda_{max}^{EtOH}$ 282 mμ ($\epsilon$=6825)

EXAMPLE 2

1,6-Dimethyl-8β-carbobenzyloxy-aminomethyl-10α-ergoline(metergoline)

2 g of 1-methyl-dihydro-D-lysergamide I was dissolved in 300 ml of anhydrous tetrahydrofuran and reacted at room temperature with about 2 g of lithium aluminum hydride. The reaction mixture was kept at room temperature for an hour; it was then refluxed for an hour and a half and thereafter about ⅔ of the solvent was distilled off.

The reaction mixture was cooled with ice and the excess reagent was destroyed slowly by addition of ice. The mixture was taken up with chloroform. The chloroform solution was washed three times with water and then distilled in vacuo. The crystalline residue was taken up with ether and filtered.

1.4 g of 1-methyl-dihydro-D-lysergamine I, melting at 145°–147° C., was obtained. 16 g of 1-methyl-dihydro-lysergamine I were dissolved in 80 ml of anhydrous pyridine by mildly heating. To the solution, cooled to −10° C. and stirred, 18 ml of 85% benzyl chloroformate (in toluene) diluted in 36 ml of chloroform were added dropwise rather rapidly. The well-stirred reaction mixture was kept at −10° C. during the addition and for 10 minutes afterwards. The cooling bath was removed and the temperature was allowed to rise to room level in about 10 minutes.

The reaction mixture was diluted with 240 ml of chloroform and rapidly washed with 80 ml of 5% aqueous sodium hydroxide solution, with saturated aqueous sodium bicarbonate solution, and finally with water.

The chloroform solution was briefly dried over anhydrous sodium sulfate and evaporated to dryness in vacuo at 40° C. The oily residue was taken up in 160 ml of benzene and passed through a column containing 48 g of alumina. The column was then eluted with a further 160 ml of benzene.

The collected eluates were evaporated in vacuo at 40° C. to give an oil that slowly crystallized by addition of ethyl ether.

After some time a crystalline mass was obtained, which was collected and washed with a small amount of benzene and diethyl ether.

12 g of white crystals were obtained, melting at 146°–148° C.; $[\alpha]_D^{28°} = -72°$ (c=0.5 in pyridine).

PHARMACOLOGY

The two compounds referred to above have proved to possess a good anti-prolactin activity in rats and a low emetic activity in dogs.

For the assessment of the anti-prolactin activity, the nidation (M. C. Shelesnyak, Am. J. Physiol., 180 47, 1955) and the lactation inhibition test (H. Tomogane et al., J. Endocr. 65, 155, 1975) have been employed, which are considered, for the ergoline derivatives, to be correlated with the prolactin-inhibiting ability.

As the reference standard Bromocriptine was used. This is well known both for its anti-nidation and anti-lactation activity in rats (E. Fluckiger and M. R. Wagner, Experientia, 24, 1130, 1968) and anti-prolactin activity (C. L. Brooks and C. W. Welsch, Proc. Soc. Exp. Biol, Med., 146, 863, 1974).

Anti-nidation activity

Adult female rats, of the Sprague-Dowley strain, in proestrus were mated with fertile males and their vaginal smears were examined the next morning.

The presence of spermatozoa was considered evidence of impregnation and onset of pregnancy (day 1).

The compounds were administered orally or intraperitoneally as methane-sulphonic salts to groups of six to eight rats on the 3rd day.

On the 14th day the animals were sacrificed and the uterus was examined for the presence of implantation sites.

The absence of implantation sites was the criterion of activity.

Several doses were tested for the $ED_{50}$ evaluation. The results are reported below in Table I.

TABLE I

| Nidation inhibition in rats | | |
|---|---|---|
| | $\cong ED_{50}$ (mg/kg) | |
| Compound | p.o. | i.p. |
| I Metergoline | 25 | 16–32 |
| II 1-Demethyl-Metergoline | 4–8 | — |
| III Bromocriptine | 8–16 | 16–32 |

Anti-lactation activity

Adult pregnant female rats were individually caged about 6 days before parturition. The day after parturition (day 1), the number of pups was adjusted to eight. The gain in weight of the litters was measured daily.

The test compounds as methane-sulfonic salts were administered orally to groups of eight mother rats on the 6th and 7th days immediately after the weighing of the litters. The control mothers were treated with the vehicle alone.

The percentage of lactation inhibition was calculated from the mean gain in weight of the litters on the 7th and 8th days in comparison with the results for the 5th and 6th days.

No lactation inhibition was present on the 7th and 8th days in the vehicle-treated (control) group.

The doses capable of reducing to 50% the gain in weight of the litters ($ED_{50}$) are reported below in Table II.

TABLE II

| Lactation inhibition in rats | |
|---|---|
| Compound | $\cong ED_{50}$ mg/kg p.o. |
| I Metergoline | 12.5–25 |
| II 1-Demethyl-metergoline | 4–8 |
| III Bromocriptine | 8–16 |

Emetic activity

The emetic activity of the compounds was examined by intravenous and oral administration to male beagle dogs weighing 15–20 kg. The compounds were administered as the methane-sulphonic salts. The animals were observed for 2 (i.v.) or 6 (p.o.) hours. Five to six animals per dose were employed for the $ED_{50}$ evaluation.

The results are reported below in Table III.

TABLE III

| Emetic activity in dogs | | |
|---|---|---|
| | $\cong ED_{50}$ (mg/kg) | |
| Compound | i.v. | p.o. |
| I Metergoline | >8 | 4–8 |
| II 1-Demethyl-metergoline | 0.05–0.1 | 0.2–0.4 |
| III Bromocriptine | 0.007 | <0.03 |

Compounds I and II, already known for their anti-serotonin activity, surprisingly show, both orally and parenterally, an anti-prolactin activity (Table I and II) of the same order as a commonly accepted reference standard (III).

On the other hand, compounds I and II are, by both routes of administration, clearly better tolerated than the reference standard III (Table III).

From the above results, one concludes that the compounds in question may find an advantageous clinical use in several therapeutic fields in which prolactin secretion is involved, viz.: inhibition of puerperal lactation, non-puerperal galactorrhoea, treatment of infertility due to hyperprolactinaemia and treatment of drug-induced hyperprolactinaemia.

Although the methane-sulphonic salts are mentioned above, other pharmaceutically acceptable salts of the kind conventionally employed in chemotherapy may be used. Among these are the hydrochloride, phosphate, sulphate, tartrate, maleate, citrate, ascorbate, succinate, salicylate, etc.

Clinical evaluation

Recent experiments suggest that serotonin (5HT) stimulates prolactin (PRL) release in animals: in man, the biological precursor of 5HT, 5 hydroxytryptophan, stimulates PRL release, this effect being partially inhibited by the antiserotonin agent methysergide.

The antiserotonin drug metergoline has recently been shown to lower basal PRL levels in normal subjects and in acromegalic patients as well as the PRL response to some provocative stimuli like Ro 4-4602 and TRH.

The invention concerns a novel method of inhibiting lactation in puerperal women by administering metergoline.

EXAMPLE

78 Healthy women who had given proof of adequate lactation following a previous pregnancy and did not want to breast-feed their babies, were studied. Metergoline was administered at a dose of 8 mg/day (4 mg at 0.800 and 4 mg at 2000) to these women: 10 women were treated with a placebo.

Five days of treatment were enough to prevent or to suppress lactation in 69 women. In the remaining 9 women, a second course of metergoline for 5 additional days, definitely inhibited every sign of mammary activity.

Metergoline, therefore, seems to be a reliable drug for inhibiting puerperal lactation being comparable in effect to the dopaminergic drug 2-Br-α-ergocriptine (bromocriptine). Moreover, it is perfectly tolerated and devoid of any side-effect. Finally, the treatment period necessary for metergoline is of 5 days in 88.5% of cases studies, while the period required for bromocriptine is of 14 days.

What is claimed is:

1. A method of inhibiting prolactin secretion in a female mammal in need of such therapy which comprises administering to the mammal an effective dose of a compound selected from the class consisting of 6-methyl-8β-carbobenzyloxy-aminomethyl-10α-ergoline, 1,6-dimethyl-8β-carbobenzyloxy-aminomethyl-10α-ergoline, and pharmaceutically acceptable acid addition salts thereof.

* * * * *